(12) United States Patent
Laurence (10) Patent No.: US 6,919,556 B1
(45) Date of Patent: Jul. 19, 2005

(54) SYSTEM AND METHOD FOR MONITORING AND EVALUATING SOLID AND SEMI-SOLID MATERIALS

(75) Inventor: George Laurence, Lafayette, IN (US)

(73) Assignee: Monocle Technologies, Inc., Lafayette, IN (US)

( * ) Notice: Subject to any disclaimer, the term of this patent is extended or adjusted under 35 U.S.C. 154(b) by 0 days.

(21) Appl. No.: 10/373,157

(22) Filed: Feb. 24, 2003

Related U.S. Application Data

(60) Provisional application No. 60/358,795, filed on Feb. 22, 2002.

(51) Int. Cl.[7] .............................. G01V 8/00; H01J 40/14

(52) U.S. Cl. ...................... 250/222.2; 250/309; 209/577

(58) Field of Search ........................... 250/222.2, 559.2, 250/559.45, 309, 223 R; 356/237.1, 237.2, 301, 394; 378/57; 209/577, 589, 576

(56) References Cited

U.S. PATENT DOCUMENTS

| | | | |
|---|---|---|---|
| 5,085,510 A | 2/1992 | Mitchell | |
| 5,094,786 A | 3/1992 | Nagashima et al. | |
| 5,638,657 A | 6/1997 | Archer et al. | |
| 6,067,154 A | * 5/2000 | Hossain et al. | 356/237.2 |
| 6,324,253 B1 | 11/2001 | Yuyama et al. | |
| 2002/0012118 A1 | 1/2002 | Worster et al. | |
| 2002/0048610 A1 | 4/2002 | Cima et al. | |
| 2002/0109110 A1 | 8/2002 | Some et al. | |
| 2002/0125434 A1 | 9/2002 | Folestad et al. | |
| 2002/0177167 A1 | 11/2002 | Levinson et al. | |

OTHER PUBLICATIONS

Inspection Machines ATI and ACI, [online], [retrieved on May 22, 2003]. Retrieved from the Internet <URL: http://www.seidenader.de/2-SE-e/+2-Progr-ATI-b.html>.

Inspection Machine PI/PI-B, [online], [retrieved on May 16, 2003]. Retrieved on the Internet <URL: http://www.seidenader.de/2-SE-e/+2-Progr-PI-b.html>.

System Inspects Blister Pack Reliably and Economically, [online], [retrieved on May 16, 2003]. Retrieved from the Internet <URL: http://devicelink.com/pmpn/archive/98/03/007.html>.

Expanding Vision's Line of Sight, [online], [retrieved on May 16, 2003]. Retrieved from the Internet <URL: http://www.devicelink.com/pmpn/archive/01/10/001.html>.

Inspecting Machines, Packaging Support Specialty Equipment, [online], [retrieved on May 16, 2003]. Retrieved from the Internet <URL: http://www.packexpo.com/ve/38995/main.html>.

Inspecting Blister Packs with NIR, [online], [retrieved on May 16, 2003]. Retrieved from the Internet <URL: http://www.packagingdigest.com/articles/200203/64.html>.

(Continued)

*Primary Examiner*—Thanh X. Luu
*Assistant Examiner*—Seung C. Sohn
(74) *Attorney, Agent, or Firm*—Rader, Fishman & Grauer PLLC (57) ABSTRACT

An system and method for monitoring and evaluating solid and semi-solid materials. In an embodiment adapted for pharmaceutical manufacturing, a rotating platter is provided which contains a plurality of chutes. Manufactured items from an earlier section of the manufacturing process are deposited upon the rotating platter, and are separated for analysis by the plurality of chutes. Mounted near the edge radius of the platter is a Raman probe, which focuses photons from a laser onto each of the manufactured items. The manufactured items radiate photons according to Raman scattering principles, which are collected by the Raman probe and analyzed by a computer against a template file. The computer operates upon the chutes to sort and release the manufactured items according to a criteria. Thus, an in-process monitoring and evaluation system may be utilized to inspect and sort manufactured items in real time.

17 Claims, 7 Drawing Sheets

OTHER PUBLICATIONS

Antaris® FT–Near Infrared Tablet Analyzer, [online], [retrieved on May 16, 2003]. Retrieved from the Internet <URL: http://www.thermo.com/eThermo/CDA/Products/Product_Detail/1.1075.17087–104–X.00.html>.

Raman Spectroscopy, [online], [retrieved May 16, 2003]. Retrieved from the Internet <URL: http://www.iyhoriba.co.uk/iy/raman/images/polymerizationmonitoring.pdf>.

Raman Without Compromise, [online], [retrieved May 16, 2003]. Retrieved from the Internet <URL: http://www.avaloninst.com>.

ChemImage Corp.,–FALLON Raman Chemical Imaging Microscope, [online], [retrieved May 16, 2003]. Retrieved from the Internet <URL: http://www.chemimage.com/products>.

In situ and on–line RAM on spectroscopy to the analysis of semiconductor heterostructures from ZnSxSel–x and group iii–nitrides, [online], [retrieved on May 16, 2003]. Retrieved from the Internet: Electronically Translated from German using Google translation service <URL: http://translate.google.com/translate?hl =en&sl=de&u=http://archiv.tu–chemnitz.de/pub/2002/0036/&prev=/Search%3Fq%3Donline%2BRaman%26hl%3Den%26lr%3D%26ie%3DUTF–8%26oe%3DUTF–8%26sa%3DG>.

Analytical Spectral Devices Near—Infrared Analyzers QualitySpec, [online], [retrieved May 23, 2003]. Retrieved from the Internet <URL: http://www.asdi.com/asdi_t2_pr_ne_qs.html>.

Pharmaceutical Inspection System, as seen in Medical Equipment Designer—Lasers & Optics, [online], [retrieved May 23, 2003]. Retrieved from the Internet <URL: http://manufacturingcenter.com/med/archives/0797/797prdspt.html>.

* cited by examiner

SYSTEM AND METHOD FOR MONITORING AND EVALUATING SOLID AND SEMI-SOLID MATERIALS

This application claims the benefit of U.S. Provisional Application No. 60/358,795, filed Feb. 22, 2002, the disclosure of which is incorporated herein by this reference.

BACKGROUND

Pharmaceutical manufacturers employ several forms for therapeutic compound delivery. For example, a liquid form may be used for injectable or ingestible therapeutic compounds. Ingestible compounds also may be delivered through tablets, capsules, and gelcaps. It is common in the manufacture of each of these forms of therapeutic compound delivery to require discrete analysis of samples of the therapeutic compound delivery form. This analysis is presently performed in a quality assurance laboratory located away from the manufacturing area. Such "off-line" analysis often is expensive and inefficient.

To illustrate the inefficiency of off-line quality assurance analysis, consider the manufacture of the tablet form of therapeutic compound delivery. During manufacture of tablets, a pharmaceutical tablet press operates on a therapeutic compound, normally in the form of a powder. The tablet press compresses the therapeutic compound into a tablet for subsequent ingestion and delivery of the therapeutic compound. Optionally, a binding agent may be added to the therapeutic compound during manufacturing to enhance tablet formation. Automated tablet presses may be employed to create tablets very quickly. Many automated tablet presses are capable of producing in excess of ten thousand tablets per minute.

After manufacture, it is typical that a representative sample of the tablets from each manufactured lot is taken to a separate quality assurance laboratory for analysis. Testing of the sample tablets ordinarily occurs after all tablets in a manufactured lot have been created, to permit a representative sample to be selected for analysis. The quality assurance laboratory conducts tests on the tablets to determine, for example, the chemical composition, variability, and other data from the sample tablets. The data collected from the tests is analyzed, and if the sample tablets are found to be within the manufacturer's specifications, the balance of the lot of manufactured tablets are released for packaging and use. If the sample tablets are not found to satisfy the manufacturer's specifications, it frequently is necessary to scrap the entire manufactured lot of the tablets.

During the time the sample tablets undergo testing in the quality assurance laboratory, the balance of the manufactured tablets from the lot are waiting in inventory storage. Without assurance that the tablets are within the manufacturer's specifications, releasing the balance of the manufactured tablets from the lot for packaging would present an unacceptable risk, as well as potentially wasting expensive packaging materials and labor. In addition, in some cases the manufacturing apparatus on which the tablets were produced may not be used again until a manufactured lot has received clearance from the quality assurance laboratory. Failure of the sample tablets to meet the manufacturer's specifications may be indicative of a problem with the manufacturing apparatus, or with the overall manufacturing process.

Unfortunately, off-line testing of pharmaceutical products in a quality assurance laboratory frequently introduces a bottleneck into the manufacturing process. The tests conducted by a quality assurance laboratory usually require the sample tablets to be prepared for testing with a great deal of human intervention. The time spent preparing the sample tablets for quality assurance testing may be several orders of magnitude longer than the time spent manufacturing the tablets.

At present, two methods are most commonly used for off-line sample testing, a spectroscopic method and a wet method. The spectroscopic method emits radiation onto a sample, and analyzes radiation emitted or reflected by the sample. The spectroscopic method may be non-destructive, or may destroy or degrade the tablet, depending on the wavelength and intensity of the radiation used. The wet method involves dissolving the sample in a solvent, or mixing the sample with other chemicals. The wet method is always destructive of the sample.

In addition to the sample preparation time required, the sample tablets may also wait in a queue while the off-line quality assurance laboratory conducts testing on other manufactured lots. Ultimately, the off-line testing process may add days or weeks to the manufacturing cycle time for each lot of tablets, through time directly spent testing the tablets, or time the sample tablets spend in queue. During this time, the balance of the manufactured tablets from the lots is held in storage, and the entire manufacturing process may be stopped, both of which can result in a significant loss of potential profit.

Further, even if the number of sample tablets selected for quality assurance testing is statistically appropriate, selectively testing only a subset of tablets taken from a larger group always incurs a risk that a problem may be overlooked. However, because the tests conducted on the sample tablets by the quality assurance laboratory ultimately results in the destruction of the tablets in many cases, it would be impossible to conduct testing on all of the manufactured tablets using common methods. The risk may be reduced by testing a greater number of the tablets, but the point at which destructive testing is economically infeasible is reached well before a one hundred percent sampling of the overall manufactured lot occurs.

Of course, the bottleneck presented by the off-line quality assurance laboratory is not limited to the manufacture of tablets. Gelatin capsules, topical ointments, and liquids are just a few possible forms of delivery of therapeutic compounds. In each case, representative samples are taken from the manufacturing process, and off-line testing is performed by a quality assurance laboratory. Therefore, it is possible that the manufacturing process for each method of therapeutic compound delivery suffers from the same or similar limitations as that experienced by the off-line analysis of tablets in a quality assurance laboratory.

For all the foregoing reasons, there is a need in the art for a system having the ability to analyze samples of pharmaceutical products in real time and in a way that is integrated with the manufacturing process. Such a system will conduct the analysis in a non-destructive manner, and will be adaptable to test each tablet produced by the manufacturing process, thereby reducing the statistical risk incurred by testing only a subset of the tablets. Alternatively, an enhanced statistical sampling could be conducted based on the information received by the system. By sampling "in-process" and in real time, process problems or manufacturing apparatus problems may be identified and fixed without requiring an entire lot to be created, thereby reducing costs.

Such a system may be used in conjunction with a traditional quality assurance laboratory. Routine testing could be done in real time using the desired system, and the quality assurance laboratory could be used to check smaller samples, to verify the correct operation of the system. Also, the desired system will provide a sufficient level of testing so that the balance of tablets from a manufactured lot may be more quickly released for packaging, and the manufacturing apparatus may be more quickly brought back into productive use, while previous lots wait in the queue or undergo analysis by the off-line quality assurance laboratory. Reducing cycle time in this critical stage of manufacturing results in less downtime, and an increase in productivity and profitability.

SUMMARY

The invention relates to a system for using spectroscopy to provide in-process quality assurance data for manufacturing processes. Such in-process data is advantageous for many reasons, and such a system would be useful for any industry producing non-metallic materials. The system is particularly advantageous for monitoring safety and quality of ingestible or injectable materials, such as those that are produced by the pharmaceutical industry.

In an embodiment, the present invention comprises a system for monitoring solid and semi-solid materials. The materials may comprise manufactured pharmaceuticals. A photon source is operable to produce substantially monochromatic photons of a predetermined wavelength. A Raman probe in communication with the photon source is operable to direct the substantially monochromatic photons produced by the photon source onto a target, thereby illuminating at least a portion of the target with the substantially monochromatic photons. The Raman probe is also operable to collect radiation emitted from the target following exposure of the target to the substantially monochromatic photons. A material handling apparatus is operable to receive a material and to consistently orient the material so that at least of portion of the material is in a position so that it will be illuminated by the substantially monochromatic photons directed by the Raman probe. The material handling device accomplishing the receipt and orientation of the material without the need for human contact with the material. An optical receiver in communication with the Raman probe is operable to receive information from the Raman probe and record a digital image of the information, the information comprising the radiation emitted from the target. A computer is in communication with the photon source, the Raman probe, the material handling apparatus, and digital image receiver, and the computer is operable to control the operation of the photon source, the Raman probe, the material handling apparatus, and the digital image receiver, and the communication therebetween.

In another embodiment, the present invention comprises a nondestructive material inspection system employing Raman spectroscopy in the inspection of a material. The material may comprise a manufactured pharmaceutical. A Raman probe is operable to direct substantially monochromatic photons onto a target thereby illuminating at least of portion of the target with the substantially monochromatic photons. The Raman probe also is operable to collect radiation emitted from the target following exposure of the target to the substantially monochromatic photons, the radiation being indicative of the target. A material handling apparatus is positioned to receive a plurality of discrete units of the material produced by a manufacturing apparatus and to orient each of the plurality of discrete units so that at least a portion of each of the plurality of discrete units will be illuminated individually by the substantially monochromatic photons directed by the Raman probe. The material handling device accomplishes the receipt and consistent orientation of the plurality of discrete units without the need for human contact with the plurality of discrete units.

In an aspect of this embodiment, a computer is in communication with the Raman probe and the material handling apparatus. The computer is adapted to control the operation of the Raman probe and the material handling apparatus, and the communication therebetween. A database is associated with the computer. The database comprises information about a desired radiation spectrum that is expected to be emitted from each of the plurality of discrete units of the material after illumination by the substantially monochromatic photons. Software is operating on the computer and is able to compare the information about the desired radiation spectrum retrieved from the database with information about an observed radiation spectrum that is emitted from a sample of the plurality of discrete units of the material that is exposed to the substantially monochromatic photons.

In still another embodiment, the present invention comprises a material handling apparatus for use in quality control application in a manufacturing system. The manufacturing system may comprise a pharmaceutical manufacturing system. A Raman probe is operable to direct substantially monochromatic photons onto a discrete unit of a target material, thereby illuminating at least of portion of the discrete unit of the target material with the substantially monochromatic photon. The Raman probe is further operable to collect radiation emitted from the discrete unit of the target material following exposure of the discrete unit of the target material to the substantially monochromatic photons, wherein the radiation is indicative of the discrete unit of the target material. A plurality of control gates automatically controls the positioning of a plurality of the discrete units of the target material produced in the manufacturing system. At least one of the plurality of control gates is operable to position each of the discrete units of the target material so that at least a portion of each of the discrete units of the target material will be illuminated individually by the substantially monochromatic photons directed by the Raman probe. At least two onward processing apparatuses are positioned to receive the discrete units of the target material after illumination of each of the discrete units of the target material by the substantially monochromatic photons directed by the Raman probe. Each of the discrete units of the target material is selectively delivered to one of the onward processing apparatuses by the control gates according to an evaluation of the radiation emitted from the discrete units of the target material. The selective delivery of each of the discrete units of the target material is accomplished without human contact with the plurality of discrete units of the target material.

In an aspect of this embodiment, a computer is in communication with the Raman probe and the material handling apparatus. The computer is adapted to control the operation of the Raman probe and the material handling apparatus, and the communication therebetween. A database is associated with the computer. The database contains information about a desired radiation spectrum that is expected to be emitted from a discrete unit of the target material after exposure of the discrete unit of the target material to the substantially monochromatic photons. Software operating on the computer is operable to compare the information about the desired radiation spectrum retrieved from the database with information about an observed radiation that is emitted from a sample of the target material that is exposed to the substantially monochromatic photons.

Yet another embodiment of the present invention comprises a computerized quality control system. A database associated with a computer contains information about a desired radiation spectrum that is expected to be emitted from a discrete unit of a material after exposure of the discrete unit of the material to monochromatic light of a predetermined wavelength. The material may comprise a manufactured pharmaceutical. Software operating on the computer is operable to compare the information about the desired radiation spectrum retrieved from the database with information about an observed radiation spectrum that is emitted from a sample of the material that is exposed to the monochromatic light of the predetermined wavelength. A Raman probe in communication with the computer is operable to collect the observed radiation emitted from the sample of the material after it is exposed to the monochromatic light of the predetermined wavelength, and to communicate an image of the observed radiation to the computer. A material handling apparatus in communication with the computer and operating cooperatively with the Raman probe automatically orients the sample of the material for exposure to the monochromatic light.

In an aspect of this embodiment of the present invention, the computerized quality control system also comprises at least two onward processing apparatuses positioned to receive the sample of the material from the material handling apparatus. The sample of the material is selectively delivered to one of the onward processing apparatuses by the material handling apparatus according to an evaluation of the observed radiation emitted from the sample of the material. The selective delivery of the sample of the material is accomplished without human contact with the sample of the material.

Still another embodiment of the present invention comprises a method for monitoring solid and semi-solid materials without the need for human contact with the materials. The method comprises the steps of receiving a plurality of materials to be monitored into a material handling apparatus; individually orienting each of the plurality of the materials; individually illuminating each of the plurality of the materials by substantially monochromatic photons; recording radiation emitted from each of the plurality of the materials after each of the plurality of the materials have been individually illuminated by the substantially monochromatic photons; comparing, with a computer, the recorded radiation with predetermined information previously stored in a memory of the computer, and selectively delivering each of the plurality of the materials from the material handling apparatus in accordance with the comparison. In an aspect of this embodiment, the materials comprise manufactured pharmaceuticals.

These and other features and advantages of the present invention, and the manner of attaing them, will be more apparent and better understood by reference to the following descriptions of embodiments of the invention taken in conjunction with the accompanying drawings and with the appended claims.

DETAILED DESCRIPTION

The present invention comprises a system and method for monitoring and evaluating solid and semi-solid materials. For the purposes of promoting an understanding of the principles of the present invention, reference will now be made to the embodiment illustrated in the drawings, and specific language will be used to describe the same. It will nevertheless be understood that no limitation of the scope of the invention is thereby intended.

Figure 1:
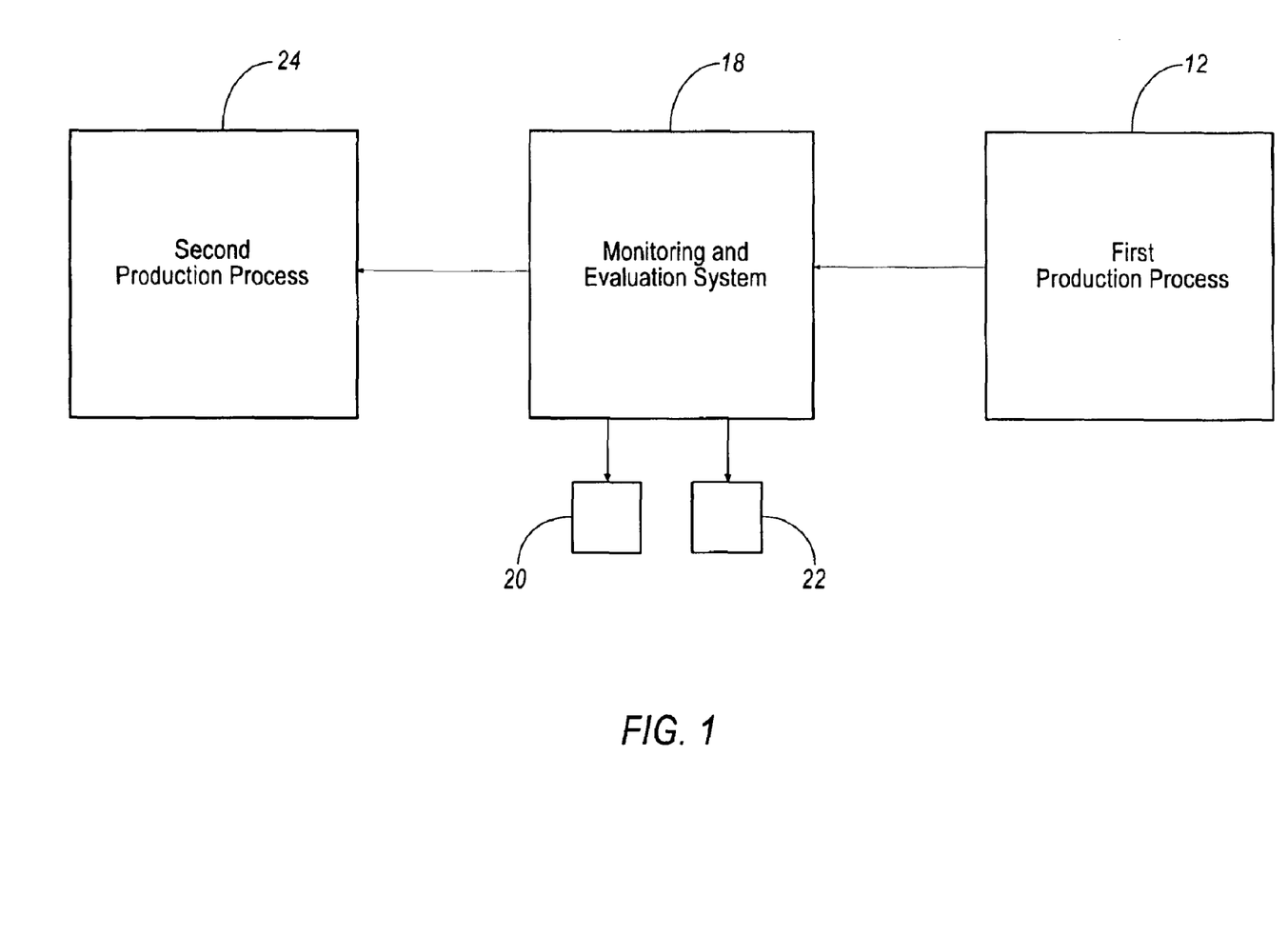
FIG. 1 shows a block diagram illustrating a portion of an exemplary manufacturing system, which includes an embodiment of the present invention.

With reference to FIG. 1, there is shown a block diagram illustrating a portion of an exemplary manufacturing system, which may be a pharmaceutical manufacturing system, comprising first production process 12, monitoring and evaluation system 18, first and second quality control processes 20 and 22, respectively, and second production process 24. In operation of this exemplary manufacturing system, materials are received from first production process 12 by monitoring and evaluation system 18, and then evaluated by monitoring and evaluation system 18 for conformance to quality assurance standards. It also is contemplated to be within the scope of the present invention that a cache of previously manufactured materials is provided to monitoring and evaluation system 18, instead of such materials being received directly from first production process 12.

Materials failing to satisfy the quality assurance standards according to the evaluation by monitoring and evaluation system 18 may be diverted to first quality control process 20 and/or second quality control process 22. For example, where the quality assurance standards comprise a specified tolerance range for the materials, materials falling below the tolerance range may be diverted to first quality control process 20, with other "under specification" materials. Similarly, materials exceeding the tolerance range may be diverted to second quality control process 22, with other "over specification" materials. Materials meeting the quality assurance standards are allowed to proceed to second production process 24 for further processing.

In an implementation of the present invention, first production process 12 may comprise a pharmaceutical tablet press of a type known in the art that is capable of producing tablets at a high rate, and second production process 24 may comprise a packaging process wherein acceptable tablets are packaged for shipment. As discussed in more detail hereinafter, an embodiment of monitoring and evaluation system 18 employed in this implementation uses optical spectroscopy to obtain information about the therapeutic compound in each of the plurality of tablets. The information regarding the therapeutic compound in each of the plurality of tablets then is compared to a quality assurance standard that is automatically accessible by monitoring and evaluation system 18.

The quality assurance standards used according to the present invention may contain information regarding a tolerance range for the amount of therapeutic compound in a tablet. If a manufactured tablet is found by monitoring and evaluation system 18 to contain an amount of therapeutic compound falling outside the specified tolerance range, further processing of the tablet is prevented. Conversely, tablets found by monitoring and evaluation system 18 to contain an amount of therapeutic compound falling within the tolerance range are allowed proceed to second production process 24. Where the tolerance range has a specified lower limit and a tablet is found by monitoring and evaluation system 18 to contain an amount of therapeutic compound falling below the lower tolerance limit, monitoring and evaluation system 18 may be adaptable to move the tablet into first quality control process 20, with other "under specification" tablets. Where a tablet is found by monitoring and evaluation system 18 to contain an amount of therapeutic compound falling above a specified upper tolerance limit, monitoring and evaluation system 18 may be adaptable to move the tablet into second quality control process 22, with other "over specification" tablets. Of course, it is contemplated to be within the scope of the present invention that other manufacturing processes and quality control processes may be used, and it also should be noted that monitoring and evaluation system 18 is not limited to evaluating tablets in a pharmaceutical manufacturing process. Indeed, a monitoring and evaluation system according to the present invention may be employed to monitor and evaluate any nonmetallic material. Also, it is contemplated to be within the scope of the present invention that any number of quality control processes may be utilized to sort non-conformiing and conforming materials, or if no quality control processes are used, that the present invention may be used to monitor a production process without separating materials into nonconforming and conforming groups.

Figure 2:
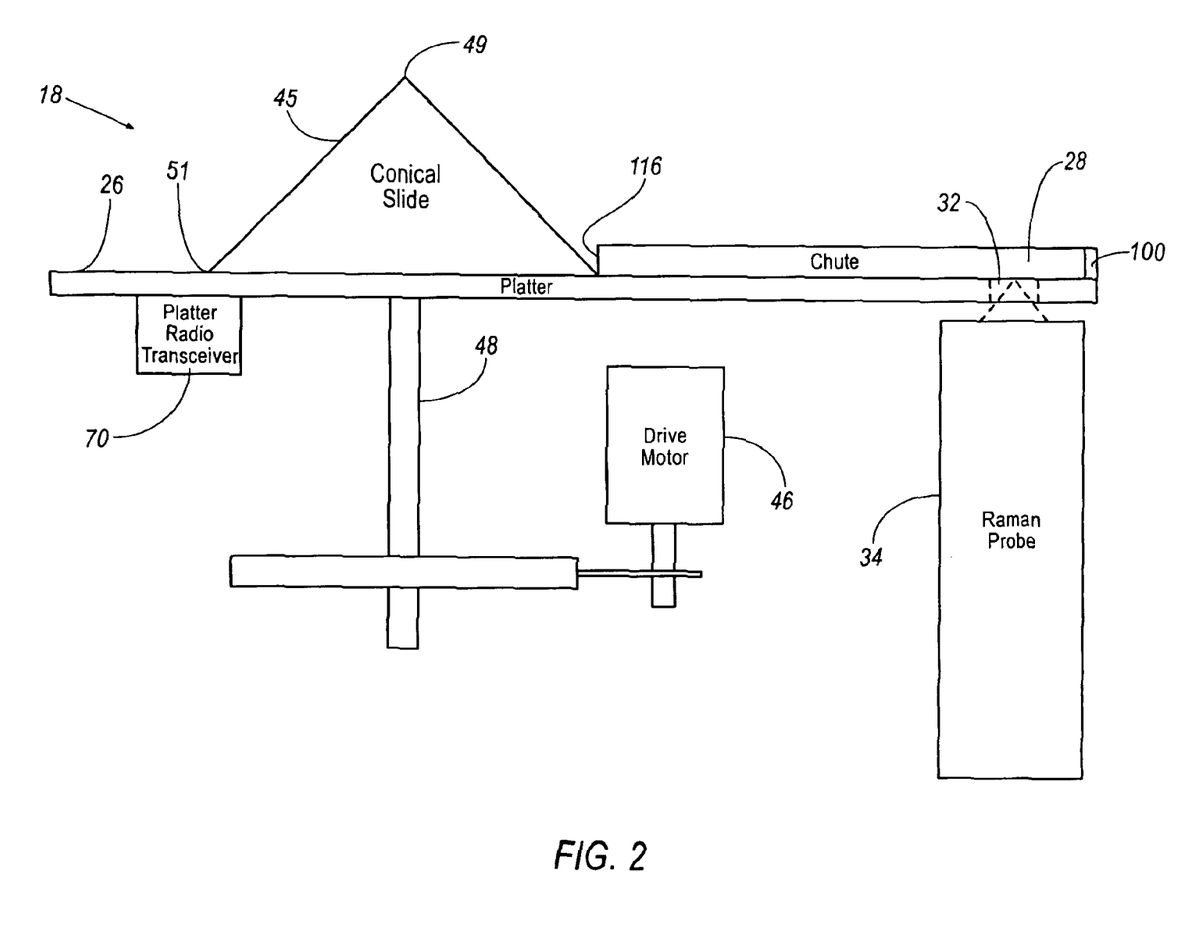
FIG. 2 shows a side view illustrating a cross-section of a portion of a monitoring and evaluation system according to an embodiment of the present invention.

With reference to FIG. 2, there is shown a side view illustrating a cross-section of a portion of a monitoring and evaluation system 18 according to an embodiment of the present invention. As shown in FIG. 2, monitoring and evaluation system 18 comprises rotating platter 26, Raman probe 34, drive motor 46, and platter radio transceiver 70.

Rotating platter 26 is substantially circular, and may be sized according to the needs of a particular practitioner of the present invention. These needs may include, for example, the therapeutic delivery form, and the size and quantity thereof. Thus, for example, in an implementation of the present invention wherein monitoring and evaluation system 18 is used in the inspection of tablets, rotating platter 26 may be sized to hold tens or hundreds of tablets simultaneously. Rotating platter 26 comprises conical slide 45 and a plurality of substantially identical chutes 28 (for purposes of clarity, only one chute 28 is shown in FIG. 2). Conical slide 45 comprises apex 49 and base 51. Each chute 28 comprises optical port 32, exit gate 100, and open end 116. The open end 116 of each of the plurality of chutes 28 adjoins base 51 of conical slide 45. The angular rotation of rotating platter 26, the number of chutes 28, and the size of chutes 28 may be adapted so that a continuous supply of tablets may be received for analysis by monitoring and evaluation system 18.

Drive motor 46 is mounted below rotating platter 26 and is connected to rotating platter 26 by drive shaft 48, such that rotation of drive shaft 48 by drive motor 46 translates into a rotation of rotating platter 26. Drive motor 46 is in communication with computer 44 (not shown in FIG. 2), such that computer 44 may cause drive motor 46 to rotate drive shaft 48 at a variable angular speed and direction. It is envisioned that drive motor 46 may operate on drive shaft 48, and thus on rotating platter 26, to rotate rotating platter 26 with a substantially constant angular velocity. Drive motor 46 may be an electric motor of a type known in the art, or may be powered by another means as would occur to one of ordinary skill in the art.

Raman probe 34 comprises a spectroscopic probe of a type known in the art adapted for Raman spectroscopy. In the embodiment of monitoring and evaluation system 18 shown in FIG. 2, Raman probe 34 is mounted below rotating platter 26 such that the focusing lenses and radiation sensor(s) of Raman probe 34 are oriented in the direction of rotating platter 26. It is contemplated to be within the scope of the present invention that Raman probe 34 is mounted above or beside rotating platter 26.

Platter radio transceiver 70 is a radio transceiver of a type known in the art capable of transmitting and receiving data at one or more predetermined frequencies. Platter radio transceiver 70 is mounted to the underside of rotating platter 26. Accordingly, platter radio transceiver 70 orbits drive shaft 48 as rotating platter 26 rotates.

Figure 3:
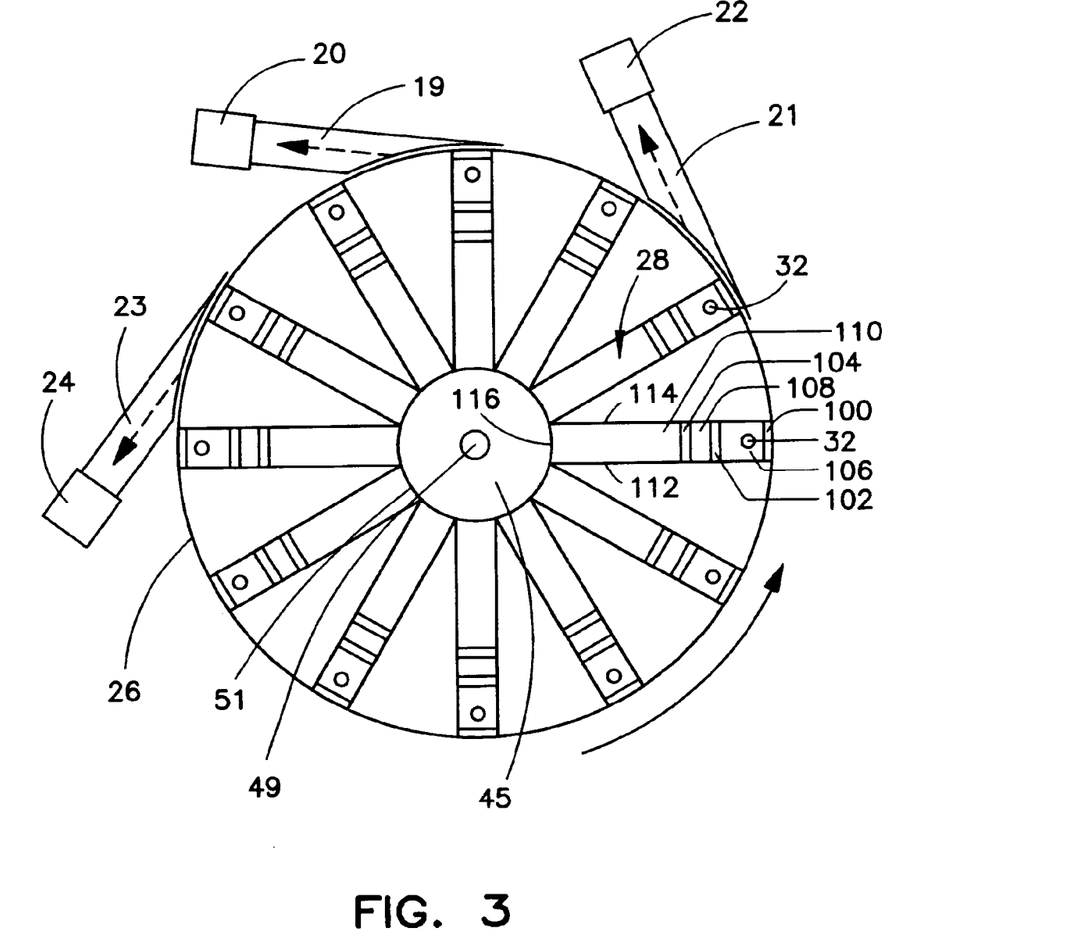
FIG. 3 shows a top view of a rotating platter of a monitoring and evaluation system according to an embodiment of the present invention.

With reference now to FIG. 3, there is shown a top view of rotating platter 26 of monitoring and evaluation system 18 according to an embodiment of the present invention. Shown in FIG. 3 are conical slide 45 comprising apex 49 and base 51, and a plurality of chutes 28 extending radially from base 51 of conical slide 45. Each chute 28 comprises open end 116 adjacent to base 51, and exit gate 100 that is substantially conterminous with the circumference of rotating platter 26. The open ends 116 of the plurality of chutes 28 are arranged side-by-side wherein the end of the first radial wall 112 of a chute 28 abuts the end of the second radial wall 114 of an adjacent chute 28. In this arrangement, materials moving down conical slide 45 (as discussed hereinafter) move into one of the plurality of chutes 28 through the plurality of side-by-side open ends 116. In the embodiment shown in FIG. 3, substantially all of the circumference of base 51 adjoins the plurality of open ends 116 of the plurality of chutes 28, but this adjoining arrangement is not required as long as the side-by-side arrangement of chutes 28 is provided.

Adjacent to rotating platter 26 are material handling devices 19, 21, and 23, which lead to first and second quality control processes 20 and 22, and second production process 24, respectively. Material handling devices 19, 21, and 23 are stationary. Accordingly, once during each rotation of rotating platter 26, each exit gate 100 passes by each of material handling devices 19, 21, and 23. It should be understood that although three material handling devices are shown in FIG. 3, the present invention is not so limited. Indeed, monitoring and evaluation system 18 may be used with any number of material handling devices, according to the need of a practitioner in a particular implementation of the present invention.

Figure 4:
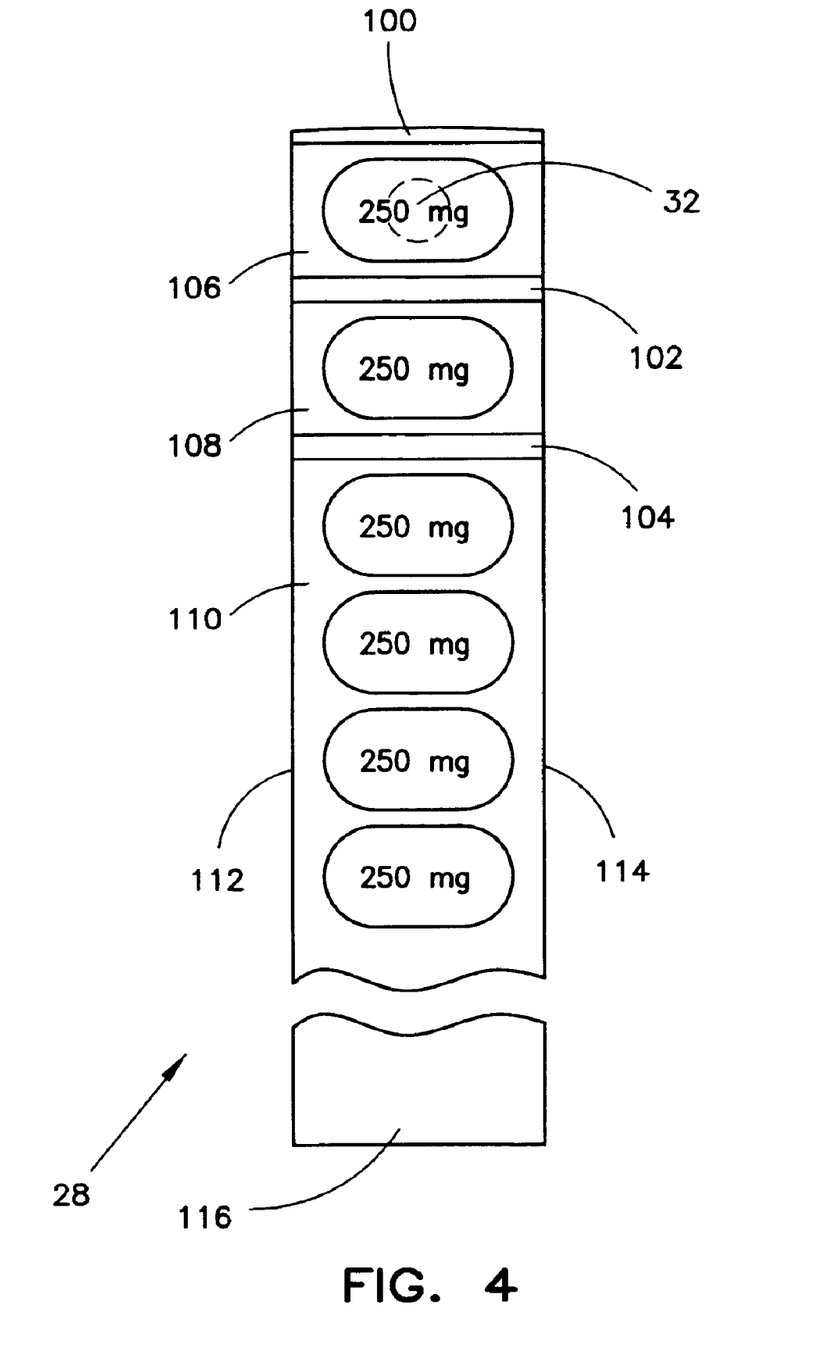
FIG. 4 shows a top view of an exemplary chute of a monitoring and evaluation system according to an embodiment of the present invention.

With reference now to FIG. 4, there is shown a top view of an exemplary chute 28 according to an embodiment of the present invention. As shown in FIG. 4, chute 28 comprises a first radial wall 112 and a second radial wall 114, wherein the first radial wall 112 and the second radial wall 114 are substantially parallel and extend from base 51 of conical slide 45 to the circumference of rotating platter 26. In an implementation of chute 28, the distance between the first radial wall 112 and the second radial wall 114 may be adjustable, so as to accommodate many shapes and sizes of samples of materials submitted for evaluation.

In the embodiment of chute 28 shown in FIG. 4, chute 28 comprises open end 116, exit gate 100, first internal control gate 102, and second internal control gate 104. Exit gate 100, first internal control gate 102, and second internal control gate 104 operate to partition chute 28 into analysis section 106, wait section 108, and a queue section 110. In the embodiment of chute 28 shown in FIG. 4, analysis section 106 and wait section 108 are sized to hold a single sample. Analysis section 106 comprises optical port 32. When optical port 32 is aligned with Raman probe 34, spectroscopic data may be obtained by Raman probe 34 from a sample that is in analysis section 106. Alternatively, a hold down device may be utilized in place of second internal control gate 104, so that a sample is restrained in queue section 110. A hold down device utilized in this way would move down (relative to platter 26) to hold a sample in place between the hold down device and the floor of chute 28.

In operation, exit gate 100, first internal control gate 102, and second internal control gate 104 move up (relative to platter 26) to close and down (relative to platter 26) to open, thereby enabling movement of items between queue section 110, wait section 108, and analysis section 106. The movement of each of exit gate 100, first internal control gate 102, and second internal control gate 104 (or, alternatively, a hold down device as previously mentioned) and, thus, the movement of items between queue section 110, wait section 108, and analysis section 106, is choreographed by computer 44 (not shown in FIG. 4). Exit gate 100, first internal control gate 102, and second internal control gate 104 may be pneumatically or electrically actuated into an open or closed position using techniques known in the art. Although the embodiment of chute 28 shown in FIG. 4 comprises two internal control gates, the present invention is not so limited. Indeed, chute 28 may have any number of internal control gates, or may utilize one or more hold down devices, according to the need of a practitioner in a particular implementation of the present invention.

Figure 5:
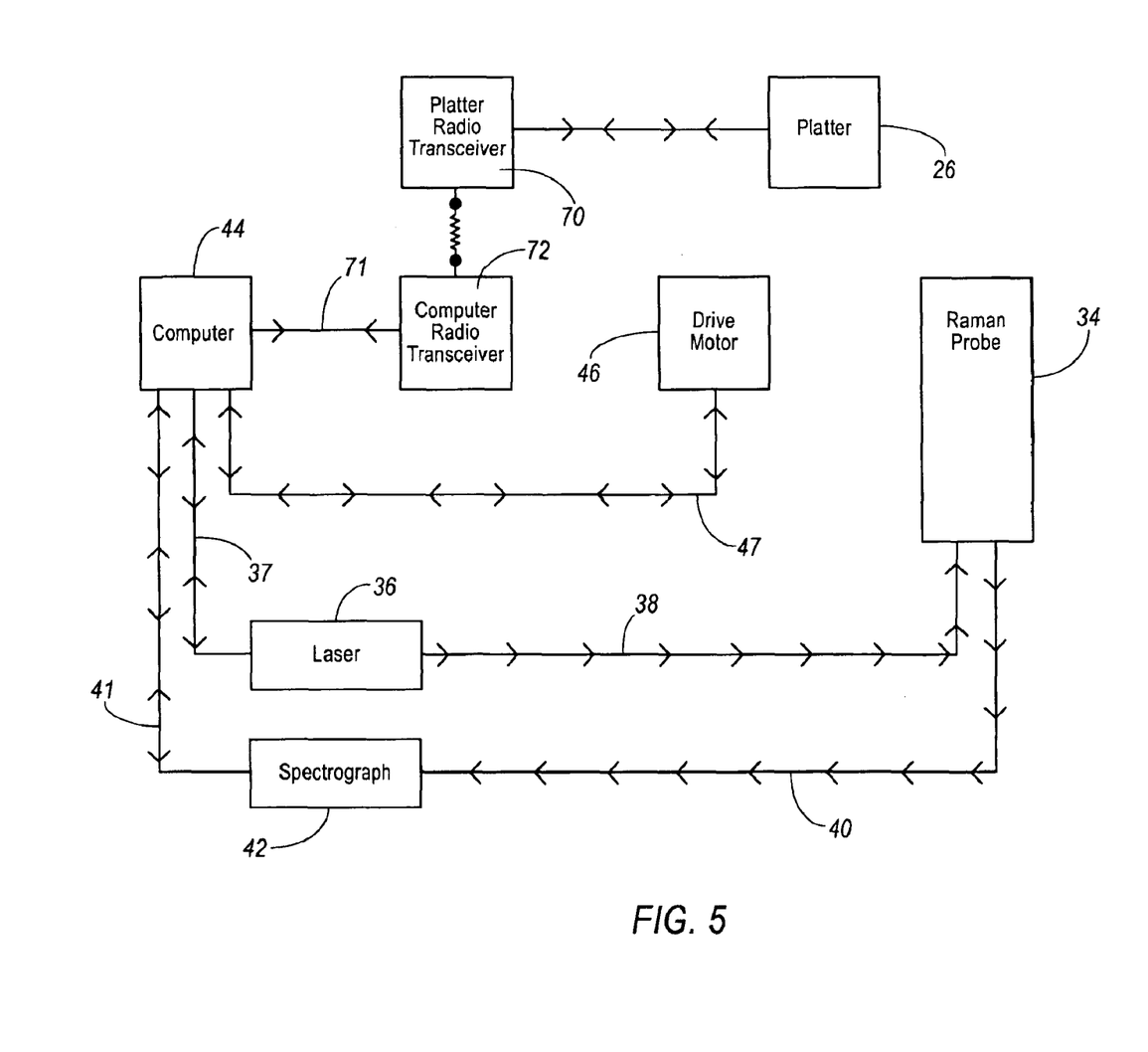
FIG. 5 shows a schematic block diagram of the analysis components of a monitoring and evaluation system according to an embodiment of the present invention.

With reference now to FIG. 5, there is shown a schematic block diagram of the analysis components of a monitoring and evaluation system according to an embodiment of the present invention. Represented in FIG. 5 are rotating platter 26, Raman probe 34, laser 36, spectrograph 42, computer 44, drive motor 46, platter radio transceiver 70, and computer radio transceiver 72.

Computer 44 is one or more computers, computing devices, or systems of a type known in the art, such as a personal computer, mainframe computer, workstation, notebook computer, laptop computer, programmable logic device, and the like. Computer 44 comprises such software, hardware, and componentry as would occur to one of skill of the art, such as, for example, one or more microprocessors, memory, input/output devices, device controllers, and the like. The configuration of computer 44 in a particular implementation of a monitoring and evaluation system comprising the present invention is left to the discretion of the practitioner.

Computer 44 is electronically interconnected with laser 36 via computer/laser communication link 37; with spectrograph 42 via computer/spectrograph communication link 41; with drive motor 46 via computer/drive motor communication link 47; and with computer radio transceiver 72 via computer/computer radio transceiver communication link 71. Such electronic interconnections may be accomplished by any means known in the art for electronically interconnecting such devices and for enabling electronic communication therebetween. Thus, it will be appreciated by those of ordinary skill in the art that such electronic interconnection may be accomplished by copper cable, coaxial cable, fiber optic cable, twisted-pair cable, wireless communication, the Internet, the commercial telephone network, one or more local area networks, one or more wide area networks, one or more wireless communications networks, the equivalents of any of the foregoing, or the combination of any two or more of the foregoing. Communication over such electronic interconnections may be accomplished by communication protocols known in the art such as, for example, serial communications, parallel communications, USB, Ethernet, packet switched protocols, and/or other communication protocols known in the art.

It is known in the Raman spectroscopy art that a given material, when illuminated with monochromatic light of a known wavelength, will emit radiation having predictable spectral features such as wavelength and intensity. Resident in the memory of computer 44 or associated with computer 44 is a database (not shown) containing the predicted spectral features for the material(s) that will be evaluated using an embodiment of a monitoring and evaluation system according to the present invention.

Laser 36 is a laser of a type known in the art that is capable of producing substantially monochromatic photons of a wavelength selected from the range of wavelengths between about 266 and about 1064 nanometers, and may be tunable to provide monochromatic photons over this range. The wavelength of photons used in a particular implementation of the present invention may be selected from this range according to the needs of the practitioner in that implememtation. In one implementation of the present invention, laser 36 produces photons with a wavelength of about 355 nanometers. In another implementation, laser 36 produces photons with a wavelength of about 532 nanometers. Techniques for production of photons at these wavelengths using lasing activity is well known in the art. In an embodiment of the present invention, laser 36 comprises a diode laser, but other laser technologies are contemplated to be within the scope of the present invention.

The substantially monochromatic photons produced by laser 36 are carried to Raman probe 34 by a first fiber optic cable 38 or other light transmission device. Raman probe 34 is operable to focus the substantially monochromatic photons onto a target material, thereby illuminating at least of portion of the target material with the substantially monochromatic photons. Raman probe 34 also is operable to collect radiation emitted from the target material following exposure of the target material to the substantially monochromatic photons.

The emitted radiation collected by Raman probe 34 is carried to spectrograph 42 via second fiber optic cable 40 or other light transmission device. Spectrograph 42 comprises a charge-coupled device ("CCD") of a type known in the art that is capable of recording a digital image of the radiation collected by Raman probe 34. Second fiber optic cable 40 emits radiation onto the CCD, which records a digital image of the wavelength and intensity of the photons. The digital image then is transmitted to computer 44 via computer/spectrograph communication link 41.

In an implementation of the present invention, spectrograph 42 comprises a CCD measuring 1×1024 pixels, wherein each pixel has a resolution of at least 16-bits. Other pixel ratios such as, for example, 64×2048 pixels, 64×512 pixels, 64×1024 pixels, and 1024×2048 pixels also may be successfully employed within the scope of the present invention.

Computer radio transceiver 72 is a radio transceiver of a type known in the art capable of transmitting and receiving data at one or more predetermined frequencies. In the embodiment of the present invention shown in FIG. 5, platter radio transceiver 70 and computer radio transceiver 72 communicate via radio frequency transmissions. Platter radio transceiver 70 and rotating platter 26 also are in communication regarding, for example, the angular position of rotating platter 26 and the status of each exit gate and control gate of each chute 28 as open or closed Operation of an embodiment of monitoring and evaluation system 18 according to the present invention will now be described with reference to FIGS. 1–6. In this embodiment, monitoring and evaluation system 18 is adapted for use with pharmaceutical tablets. Accordingly, first production process 12 comprises a tablet press of a type known in the art.

Computer 44 controls and choreographs the operations of monitoring and evaluation system 18. According to the present invention, computer 44 causes drive motor 46 to operate drive shaft 48 at a desired angular speed, which results in rotation of rotating platter 26. While rotating platter 26 is rotating in the direction indicated in FIG. 3, a plurality of tablets are deposited on apex 49 of conical slide 45. Gravity urges the plurality of tablets down the slope of conical slide 45 toward base 51 thereof At base 51 of conical slide 45, the centrifugal force generated by the rotational rotating platter 26 urges the plurality of tablets through the plurality of open ends 116 and into the plurality of chutes 28. Centrifugal force continues to act on the tablets within chutes 28, causing tablets within a chute 28 to seek a position at the distal end of the chute 28.

For purposes of clarity, the operation of chutes 28 in an embodiment of the present invention will be described with reference to only one of the plurality of chutes 28, and to a first tablet, a second tablet, and a third tablet within the chute 28, wherein the first tablet enters the chute 28 first, followed by the second tablet and then the third tablet. It will be understood that this example merely clarifies the operation of the present invention, and should not be interpreted as a limitation. It is within the scope of the present invention that tablets may be continuously received for evaluation by the present invention.

Initially, chute 28 is empty, exit gate 100 of chute 28 is closed, and first control gate 102 and second control gate 104 are open. As the first tablet fills analysis section 106, sensors (not shown) on rotating platter 26 cause first control gate 102 to close behind the first tablet, thus creating a partition between wait section 108 and analysis section 106. The first tablet is thus separated from subsequent tablets, and is positioned for analysis over optical port 32 of analysis section 106. It should be noted that analysis section 106 should be sized to be slightly larger than the tablet, so that the size of analysis section 106 in combination with the centrifugal force provided by the rotating platter 26, forces each tablet that enters analysis section 106 into consistent position within the analysis section 106, thus improving the consistency of tablet analysis.

As the second tablet reaches wait section 108, the second control gate 104 closes to create a partition between wait section 108 and queue section 110. The second tablet is thus separated from the first tablet and from subsequent tablets. The third tablet is thus located in the queue section 110, and subsequent tablets may be located in the queue section 110 as well. As described previously, second control gate 104 may alternatively comprise a hold down device used to restrain the tablets in queue section 110.

Information regarding the angular position of rotating platter 26 and the open/closed status of each exit gate and control gate of each chute 28 is continually passed to the computer 44 via radio transmissions between platter radio transceiver 70 and computer radio transceiver 72. As optical port 32 of chute 28 aligns with Raman probe 34, computer 44 communicates with laser 36 to cause laser 36 to engage in lasing activity. Monochromatic photons then are produced by laser 36 and are transmitted to Raman probe 34 via first fiber optic cable 38.

Figure 6:
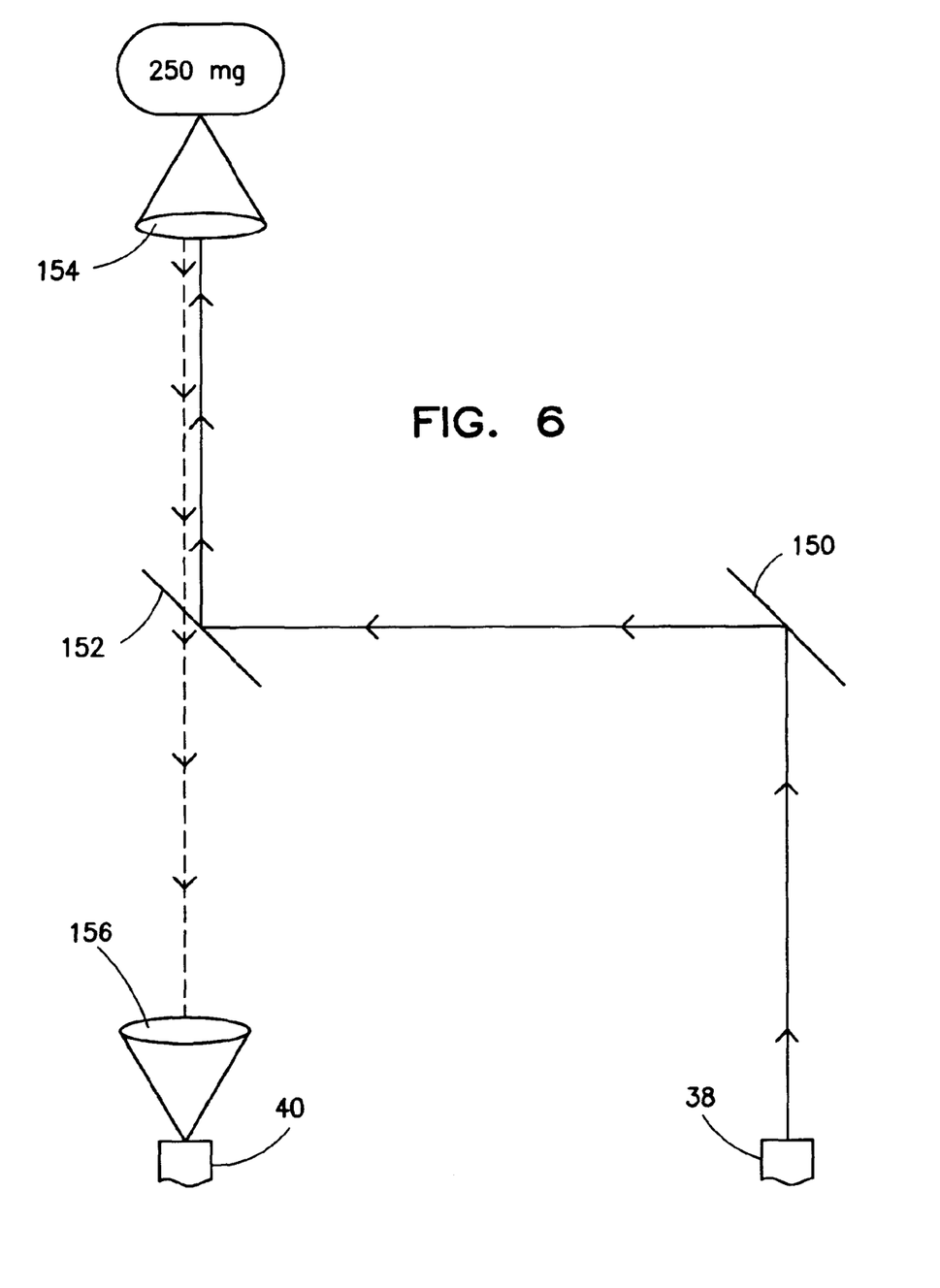
FIG. 6 shows a schematic diagram of a Raman probe as used in an embodiment of the present invention.

A schematic diagram of Raman probe 34 is shown in FIG. 6. As shown therein, Raman probe 34 comprises a first turning mirror 150, a long pass filter 152, first focusing lens 154, and a second focusing lens 156. First turning mirror 150 reflects the photons received from the first fiber optic cable 38, and is angled to reflect the photons toward long pass filter 152. Long pass filter 152 is coated with a semi-reflective material. The long pass filter 152 coating is selected to reflect light with the wavelength generated by the laser 36, and to allow radiation with a wavelength longer than the wavelength generated by the laser 36 to pass through without being reflected. The photons of the selected wavelength of the long pass filter coating are reflected by long pass filter 152 toward first focusing lens 154. When first focusing lens 154 is aligned with optical port 32 of chute 28, the photons are focused onto the tablet in analysis section 106. Long pass filter 152 may also be a holographic notch filter selected in accordance with the wavelength of the monochromatic photons generated by laser 36 in the particular implementation of the present invention.

Photons emitted by the Raman probe 34 through first focusing lens 154 strike the surface of the tablet in analysis section 106, and radiation is thereupon emitted from the tablet in a random and scattered manner. A portion of this radiation is collected and collimated by first focusing lens 154 and transmitted into the Raman probe 34. A portion of the emitted radiation then is transmitted through the long pass filter coating of the long pass filter 152, is focused by second focusing lens 156, and is received by second fiber optic cable 40, which communicates the radiation to spectrograph 42. Some reflected laser light will also pass through the long pass filter coating and be collected by second fiber optic cable 40.

Certain spectral features of the emitted radiation are recorded by the CCD of spectrograph 42, which communicates the recorded spectral features to the computer 44 over computer/spectrograph communication link 41. Residing in the memory of computer 44 is the predicted spectral feature information for a tablet of the type being analyzed. Computer 44 compares the spectral feature information recorded by spectrograph 42 to the predicted spectral feature information in the memory of computer 44. As a result of the comparison, computer 44 determines if the first tablet contains a concentration of therapeutic compound that is within the specifications for a tablet of the type being analyzed. If the tablet is found to be outside of the specifications, in this embodiment of the present invention a further determination is made as to whether the tablet contains a concentration of therapeutic compound above the threshold specification concentration, or a concentration of therapeutic compound below the threshold specification concentration. It should be noted that while the computer 44 is analyzing the spectral feature information, rotating platter 26 continues to rotate so that the first tablet may no longer be over Raman probe 34.

Based on positional information of the rotating platter 26, and the information that the first tablet is above, below, or within specification, the computer 44 operates to cause exit gate 100 to open at an appropriate time so that the centrifugal force generated by the rotation of rotating platter 26 causes the first tablet to be released to one of material handling devices 19, 21, or 23. For example, if computer 44 determines the first tablet to be below specification, computer 44 causes exit gate 100 to open in conjunction with material handling device 19, transferring the tablet to first quality control process 20. If the computer 44 determines the first tablet to be above specification, the computer 44 causes exit gate 100 to open in conjunction with material handling device 21, transferring the tablet to second quality control process 22. If the computer 44 determines the first tablet to be within specification, the computer 44 causes exit gate 100 to open in conjunction with material handling device 23, transferring the tablet to second production process 24.

After the first tablet has moved off of rotating platter 26, exit gate 100 closes. First control gate 102 then opens, and centrifugal force urges the second tablet into analysis section 106. First control gate 102 then closes, and as the size of chute 28 is only slightly larger than the diameter of the tablet, the second tablet is oriented in analysis section 106 in the same fashion as was the first tablet.

After the second tablet has moved from wait section 108 into analysis section 106, second control gate 104 closes, and centrifugal force urges the third tablet into wait section 108. Second control gate 104 closes, and centrifugal force orients the third tablet in wait section 108 similarly to the second tablet in analysis section 106. It should be noted that additional tablets maybe located in queue section 110.

Second tablet is thus oriented properly for analysis, and rotating platter 26 continues to rotate. When chute 28 aligns with Raman probe 34, spectral feature information from the second tablet will be collected, and a determination of the second tablet to be above, below, or within specification will be made similarly to the first tablet.

Figure 7:
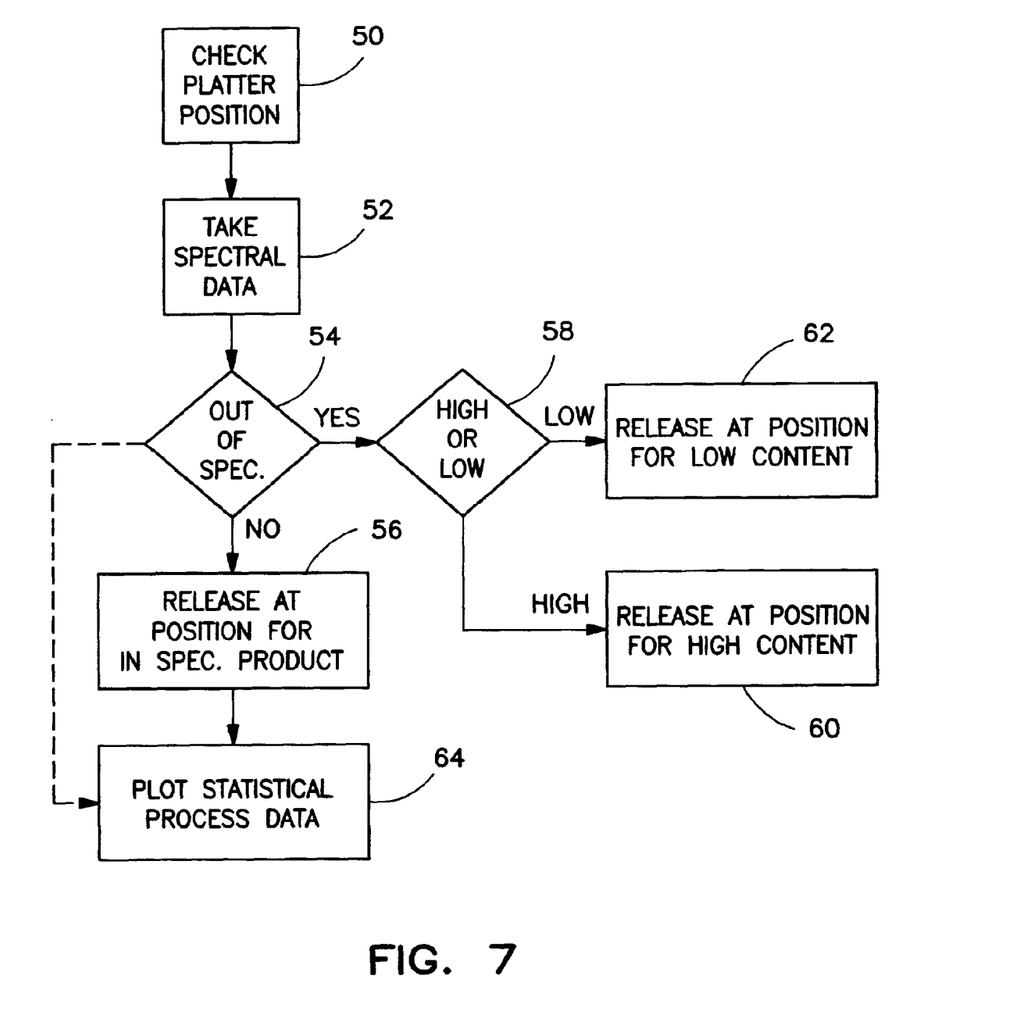
FIG. 7 shows a flow chart of the detection and determination process according to an embodiment of the present invention.

FIG. 7 shows a flow chart illustrating the detection and determination process as described above. Before the detection, the position of rotating platter must be checked (at block 50) to ensure that the tablet is properly aligned with Raman probe, then the spectral feature data is taken (at block 52). A determination of the content of the tablet based on the spectral features of the tablet, and whether the tablet is within or without specification is made (at block 54). If the tablet is within the specified tolerance range, then the tablet is released at the proper position for within specification product (at block 56). After the determination of being within or without specification, or even contemporaneously, a second determination of whether the out of specification tablets are above or below the tolerance range is made (at block 58) and the tablet then is routed accordingly (at blocks 60 and 62). In addition to the determinations made, the present invention may be utilized to plot statistical data (at block 64) regarding the process and the numbers of tablets which are within the specified tolerance range and the numbers which are outside the specified tolerance range.

It will be appreciated that the present invention provides significant advantages over the prior art. Specifically, the present invention provides the ability to analyze samples of pharmaceutical products in real time and in a way that is integrated with the manufacturing process. The present invention allows for analysis in a nondestructive manner, and is adaptable to evaluate every tablet produced by the manufacturing process, thereby reducing the statistical risk incurred by testing only a subset of the tablets. In addition, by evaluating materials "in-process" and in real time, the present invention enables process problems or manufacturing apparatus problems to be readily identified and fixed without requiring an entire lot of the material to be created, thereby reducing costs.

The present invention may be used in conjunction with a traditional quality assurance laboratory. For example, the present invention provides a sufficient level of testing so that the balance of tablets from a manufactured lot may be more quickly released for packaging, and the manufacturing apparatus may be more quickly brought back into productive use, while other lots wait in the queue or undergo analysis by the off-line quality assurance laboratory. Reducing cycle time in this critical stage of manufacturing results in less downtime, and an increase in productivity and profitability.

While this invention has been described as having an exemplary structure, the present invention can be further modified within the scope and spirit of this disclosure. This application is therefore intended to cover any variations, uses, or adaptations of the invention using its general principles. For example, the methods disclosed herein and in the appended claims represent one possible sequence of performing the steps thereof. A practitioner of the present invention may determine in a particular implementation of the present invention that multiple steps of one or more of the disclosed methods may be combinable, or that a different sequence of steps may be employed to accomplish the same results. Each such implementation falls within the scope of the present invention as disclosed herein and in the appended claims. Furthermore, this application is intended to cover such departures from the present disclosure as come within known or customary practice in the art to which this invention pertains.

I claim:

1. A system for monitoring solid and semi-solid materials comprising:

a photon source, said photon source being operable to produce substantially monochromatic photons of a predetermined wavelength;

a Raman probe in communication with said photon source, said Raman probe operable to direct said substantially monochromatic photons produced by said photon source onto a target, thereby illuminating at least of portion of said target with said substantially monochromatic photons, said Raman probe further operable to collect radiation emitted from said target following exposure of said target to said substantially monochromatic photons;

a material handling apparatus having at least one control gate operable to receive a material and to orient said material so that at least of portion of said material is in a position so that it will be illuminated by said substantially monochromatic photons directed by said Raman probe, said material handling device accomplishing said receipt and orientation of said material without the need for human contact with said material;

an optical receiver in communication with said Raman probe, said optical receiver operable to receive information from said Raman probe and record a digital image of said information, said information comprising said radiation emitted from said target; and a computer in communication with said photon source, said Raman probe, said material handling apparatus, and digital image receiver, said computer operable to control the operation of said photon source, said Raman probe, said material handling apparatus, and said digital image receiver, and the communication therebetween.

2. The system of claim 1, further comprising:

a database associated with said computer, said database comprising information about a desired radiation spectrum that is expected to be emitted from said material after exposure of said material said substantially monochromatic photons; and software operating on said computer, said software operable to compare said information about said desired radiation spectrum retrieved from said database with information about an observed radiation spectrum that is emitted from a sample of said material that is exposed to said substantially monochromatic photons.

3. The system of claim 1, wherein said material comprises a manufactured pharmaceutical product.

4. A nondestructive material inspection system employing Raman spectroscopy in the inspection of a material, the system comprising:

a manufacturing apparatus for producing a material;

a Raman probe, said Raman probe being operable to direct substantially monochromatic photons onto a target thereby illuminating at least of portion of said target with said substantially monochromatic photons, said Raman probe being further operable to collect radiation emitted from said target following exposure of said target to said substantially monochromatic photons, said radiation being indicative of said target; and a material handling apparatus having at least one control gate, said material handling apparatus positioned to receive said a plurality of discrete units of said material produced by said manufacturing apparatus and to orient each of said plurality of discrete units so that at least of portion of each of said plurality of discrete units will be illuminated individually by said substantially monochromatic photons directed by said Raman probe, said material handling device accomplishing said receipt and orientation of said plurality of discrete units without the need for human contact with said plurality of discrete units.

5. The nondestructive material inspection system of claim 4, further comprising:

a computer in communication with said Raman probe and said material handling apparatus, said computer being adapted to control the operation of said Raman probe and said material handling apparatus, and the communication therebetween;

a database associated with said computer, said database comprising information about a desired radiation spectrum that is expected to be emitted from each of said plurality of discrete units of said material after illumination by said substantially monochromatic photons; and software operating on said computer, said software operable to compare said information about said desired radiation spectrum retrieved from said database with information about an observed radiation spectrum that is emitted from a sample of said plurality of discrete units of said material that is exposed to said substantially monochromatic photons.

6. The nondestructive material inspection system of claim 4, wherein said material comprises a manufactured pharmaceutical product, and wherein said manufacturing apparatus comprises a pharmaceutical manufacturing apparatus.

7. A material handling apparatus for use in quality control application in a manufacturing system, said material handling apparatus comprising:

a Raman probe, said Raman probe being operable to direct substantially monochromatic photons onto a discrete unit of a target material thereby illuminating at least of portion of said discrete unit of said target material with said substantially monochromatic photons, said Raman probe being further operable to collect radiation emitted from said discrete unit of said target material following exposure of said discrete unit of said target material to said substantially monochromatic photons, said radiation being indicative of said discrete unit of said target material;

a plurality of control gates automatically controlling the positioning of a plurality of said discrete units of said target material produced in said manufacturing system, at least one of said plurality of control gates being operable to position each of said discrete units so that at least a of portion of each of said discrete units will be illuminated individually by said substantially monochromatic photons directed by said Raman probe; and at least two onward processing apparatuses positioned to receive each of said discrete units after illumination of each said discrete units by said substantially monochromatic photons directed by said Raman probe, each of said discrete units being selectively delivered to one of said at least two onward processing apparatuses by said control gates according to an evaluation of said radiation emitted from said target material, said selective delivery of each of said discrete units being accomplished without human contact with said plurality of said discrete units.

8. The material handling apparatus of claim 7, further comprising:

a computer in communication with said Raman probe and said material handling apparatus, said computer being adapted to control the operation of said Raman probe and said material handling apparatus, and the communication therebetween;

a database associated with said computer, said database comprising information about a desired radiation spectrum that is expected to be emitted from each of said plurality of discrete units of said target material after illumination by said substantially monochromatic photons; and software operating on said computer, said software operable to compare said information about said desired radiation spectrum retrieved from said database with information about an observed radiation spectrum that is emitted from a sample of said plurality of discrete units of said target material that is exposed to said substantially monochromatic photons.

9. The material handling apparatus of claim 7, wherein said target material comprises a manufactured pharmaceutical product.

10. A computerized quality control system comprising:

a computer;

a database associated with said computer, said database comprising information about a desired radiation spectrum that is expected to be emitted from a discrete unit of a material after exposure of said discrete unit to monochromatic light of a predetermined wavelength;

software operable by said computer, said software operable to compare said information about said desired radiation spectrum retrieved from said database with information about an observed radiation spectrum that is emitted from a sample of said material that is exposed to said monochromatic light of said predetermined wavelength;

a Raman probe in communication with said computer, said Raman probe being operable to collect said observed radiation emitted from said sample of said material after it is exposed to said monochromatic light of said predetermined wavelength, and to communicate an image of said observed radiation to said computer; and a material handling apparatus having at least one control gate in communication with said computer and operating cooperatively with said Raman probe so that said sample of said material is automatically oriented by said material handling apparatus for exposure to said monochromatic light.

11. The computerized quality control system of claim 10, further comprising:

at least two onward processing apparatuses positioned to receive said sample of said material from said material handling apparatus, said sample of said material being selectively delivered to one of said at least two onward processing apparatuses by said material handling apparatus according to an evaluation of said observed radiation emitted from sample of said material, said selective delivery of sample of said material being accomplished without human contact with sample of said material.

12. The computerized quality control system of claim 10, wherein said material comprises a manufactured pharmaceutical product.

13. A method for monitoring solid and semi-solid materials without the need for human contact with said materials, the method comprising the steps of:

receiving a plurality of materials to be monitored into a material handling apparatus;

individually orienting each of said plurality of said materials;

individually illuminating each of said plurality of said materials by substantially monochromatic photons;

recording radiation emitted from each of said plurality of said materials after each of said plurality of said materials have been individually illuminated by said substantially monochromatic photons;

comparing, with a computer, said recorded radiation with predetermined information previously stored in a memory of said computer; and selectively delivering each of said plurality of said materials from said material handling apparatus having at least one control gate in accordance with said comparison.

14. The method of claim 13, wherein certain of said plurality of said materials are determined to be outside of a tolerance range, the method further comprising the steps of:

determining whether each of said certain of said plurality of said materials that are outside of said tolerance range fall above or below said tolerance range; and selectively releasing each of said certain of said plurality of said materials to at least one of a plurality of locations based on whether each of said certain of said plurality of said materials falls above or below said tolerance range.

15. The method of claim 13, further comprising the step of:

plotting statistical data relating to the comparison of said recorded radiation with said predetermined information previously stored in said memory of said computer.

16. The method of claim 13, wherein said materials comprise manufactured pharmaceutical products.

17. A system for monitoring solid and semi-solid pharmaceutical materials comprising:

a photon source, said photon source being operable to produce substantially monochromatic photons of a predetermined wavelength;

a Raman probe in communication with said photon source, said Raman probe being operable to direct said substantially monochromatic photons produced by said photon source onto a target, thereby illuminating at least of portion of said target with said substantially monochromatic photons, said Raman probe further operable to collect radiation emitted from said target following exposure of said target to said substantially monochromatic photons;

a material handling apparatus having a chute and at least one control gate operable to receive a material and to orient said material so that at least of portion of said material is in a position such that it will be illuminated by said substantially monochromatic photons directed by said Raman probe, said material handling device accomplishing said receipt and orientation of said material without the need for human contact with said material;

an optical receiver in communication with said Raman probe, said optical receiver operable to receive information from said Raman probe and record a digital image of said information, said information comprising said radiation emitted from said target; and a computer in communication with said photon source, said Raman probe, said material handling apparatus, and digital image receiver, said computer operable to control the operation of said photon source, said Raman probe, said material handling apparatus, and said digital image receiver, and the communication therebetween.

* * * * *